United States Patent [19]

Franetzki et al.

[11] Patent Number: 4,883,467
[45] Date of Patent: Nov. 28, 1989

[54] RECIPROCATING PUMP FOR AN IMPLANTABLE MEDICATION DOSAGE DEVICE

[75] Inventors: Manfred Franetzki, Uttenreuth; Georg Geisselbrecht, Erlangen; Gerhard Buchholtz, Erlangen; Werner Fickweller, Erlangen; Peter Obermann, Erlangen, all of Fed. Rep. of Germany

[73] Assignee: Siemens Aktiengesellschaft, Berlin and Munich, Fed. Rep. of Germany

[21] Appl. No.: 182,723

[22] Filed: Apr. 18, 1988

[30] Foreign Application Priority Data

Apr. 22, 1987 [DE] Fed. Rep. of Germany ....... 3713498

[51] Int. Cl.$^4$ ............................................. A61M 1/00
[52] U.S. Cl. ..................... 604/152; 604/249; 604/891.1; 417/274; 417/562; 417/417
[58] Field of Search ............... 128/DIG. 12; 604/121, 604/131, 134, 135, 151, 152, 181, 183, 247, 249, 218, 225, 891.1; 417/274, 562, 417; 92/60.5

[56] References Cited

U.S. PATENT DOCUMENTS 2,679,353 5/1954 Bernat et al. .................... 417/562
2,853,229 9/1958 Dolz .................................. 417/417
2,954,917 9/1958 Bayer ................................ 417/417
3,468,257 9/1969 Uofink .
3,781,140 12/1973 Gladden ........................... 417/317
4,543,989 10/1985 Lorson .
4,568,250 2/1986 Falk et al. .

FOREIGN PATENT DOCUMENTS 0103536 3/1984 European Pat. Off. .
3515848 11/1986 Fed. Rep. of Germany .
0959793 9/1982 U.S.S.R. ............................. 604/152

Primary Examiner—C. Fred Rosenbaum
Assistant Examiner—Mario Costantino

[57] ABSTRACT

A reciprocating pump suitable for use in an implantable medication dosage device has a piston movable in a chamber connected to a medication reservoir, the chamber having an output closable by a check valve. The check valve includes a movable element which is acted upon by a biasing system to urge the moveable element in a direction to close the check valve. The moveable element has a sealing surface against which an end face of the piston presses with tight adjacency as the piston moves to an extreme position during its output stroke.

11 Claims, 2 Drawing Sheets

RECIPROCATING PUMP FOR AN IMPLANTABLE MEDICATION DOSAGE DEVICE

BACKGROUND OF THE INVENTION

1. Field of the Invention

The present invention is related to a reciprocating pump capable of miniaturization for use in a medication dosage device, and in particular to such a pump which passes, i.e., is not blocked or stopped by gas bubbles which may be present in the liquid medication.

2. Description of the Prior Art

For reasons of miniaturization, it is preferable to use a reciprocating pump as the pump unit in implantable medication dosage devices such as, for example, an insulin dosage device. Such devices convey a liquid medication at low rates for delivery to a patient. The piston displacement of such a pump required for this type of use is approximately 0.5 through 1.0 microliter.

It is also preferable that such a reciprocating pump be capable of pumping gas bubbles with a satisfactory conveying rate, so that delivery of the medication does not cease given the presence of a gas bubble at some location in the fluid passage of the device, so that the patient does not remain unsupplied with medication over a longer time. Gas bubbles in the medication reservoir may arise, for example, due to gas generation within the medication, or during refilling of the medication reservoir.

The problem of gas bubble conveying or pumping is even more pronounced in a medication dosage device wherein, as is typical, the medication reservoir is charged with an underpressure, i.e., a pressure below atmospheric pressure, as in the device described in German OS No. 26 52 026. In a typical case, such underpressure in the medication reservoir, which is advantageous for safety reasons, is between 0.5 and 1.0 bar. Given an ideal pump, having a pump chamber free of dead space, the gas conveying rate may be smaller than the liquid conveying rate by a factor as large as two.

If, by contrast, the pump has dead space in the pump chamber, the dead space being the same size as the displacement volume, conveying of gas bubbles is impossible at the lower limit of the underpressure (0.5 bar). A gas bubble situated in the pump chamber under such conditions would be merely compressed and decompressed, without being transported to the output side of the device. Reliable functioning of the device is thus not guaranteed given lower underpressures. This problem usually does not arise, however, in larger pumps having a displacement volume greater than 10 $\mu$liters.

The above problem becomes acute, however, in devices which are typical of many medication dosage devices, wherein the medication reservoir is at an underpressure of 300 through 500 mbar (500–700 mbar absolute), as is used in many insulin infusion devices.

The same problem arises when pumping or conveying is undertaken against an overpressure, for example, against a substantially plugged catheter. In general terms, if there is a significant difference between the (low) input pressure and the (high) output pressure at the pump, the risk is present that no medication will be conveyed, even if the piston motion is maintained. As discussed above, the pressure difference may arise due to underpressure in the medication reservoir, or overpressure at the catheter. For many of the above reasons, it is preferable to have a ratio which is as large as possible, given other construction constraints, between the displacement volume and the dead space in the pump chamber of a reciprocating pump. This ratio is referred to as the compression ratio. Various miniaturized pumping systems have been devised by those skilled in the art in an effort to improve the compression ratio.

A reciprocating pump is disclosed, for example, in U.S. Pat. No. 4,568,250 having an input chamber formed by an end face of a housing, a cylindrical wall, and the end face of a piston. The end face of the housing has an opening connected to a reservoir. A moveable element of a check valve is disposed inside the input chamber. A mechanical spring system holds the moveable part pressed against the input opening in a rest position. This structure therefore has a relatively large dead space, having an unfavorable influence on the gas conveying capability of this system, due to the spring system and its associated fastening means.

Another reciprocating pump is described in U.S. Pat. No. 3,468,257 having a check valve disposed at the output side of the pump. This valve is also actuated by a mechanical spring system, and requires a relatively large dead space for the fluid. This structure therefore presents the same problems as discussed above in the event of the appearance of gas bubbles in the fluid to be conveyed.

German OS No. 35 15 848 discloses a valve for medication dosage devices. This valve is not used as a component part of such devices, but as an additional element which is placed in the intake line or the discharge line associated with the dosage device. In this valve, the closing force of the moveable element is magnetically generated. The moveable element may be spherical, and presses against a resilient O-ring. This valve, however, does not result in a tight placement of the moveable element against the piston of the dosage device, and would not do so even if this valve structure were to be integrated within a medication dosage device. Therefore even in the case of such integration, a relatively large dead space would also arise, thereby still presenting the same problems with respect to gas bubble pumping as discussed above.

An embodiment as descirbed in FIG. 3 of European Application No. 0 103 536 showing a reciprocating pump with an integrated check valve. The check valve is disposed at the output side of the pump. This pump has a piston moveable in a cylinder. There is no sealing closure between the piston and the cylinder wall, so that movement of the piston in a first direction displaces the medium to be conveyed in an output direction, and the device is simultaneously charged with fresh medium from a reservoir connected thereto. The piston speed is selected such that the medium does not entirely flow through the gap between the piston and the cylinder wall given the presence of an opposing pressure. When the piston moves in a second, opposite direction, the pump chamber is again filled by medium flowing through the gap between the piston and the cylinder wall. The check valve is formed by a resilient membrane which terminates a longer channel. Again, difficulties and the potential for malfunction arise if gas bubbles are contained in the medium.

SUMMARY OF THE INVENTION

It is an object of the present invention to provide a reciprocating pump suitable for use in an implantable medication dosage device which is reliably operable in the presence of gas bubbles in the liquid to be conveyed.

It is a further object of the present invention to provide such a reciprocating pump which conveys or pumps gas bubbles which may be present in the liquid to be conveyed at a rate which is not substantially reduced in comparison to the conveying rate for liquid free of gas bubbles.

The above objects are achieved in a reciprocating pump for a medication dosage device wherein, instead of increasing the displacement volume of the pump, the dead space within the pump is substantially reduced or avoided.

Significant reduction in the dead space of the reciprocating pump constructed in accordance with the principles of the present invention is achieved by disposing a check valve having a moveable element at an output of the pump, the moveable element of the check valve having a sealing surface against which an end face of the piston presses with tight adjacency as the piston approaches its extreme position of the output stroke.

The sealing surface is preferably relatively thin, i.e., it has a small dimension in the axial direction. For this reason, if the sealing surface and the end face of the piston are ideal planar surfaces, there may be difficulty in the surfaces detaching from each other upon transistion of the piston from its extreme output stroke position to the return stroke. To avoid such difficulty, in one embodiment either the end face of the piston, or the sealing surface, or both surfaces, have a small non-planar region. This region may be a depression in one or both surfaces, such as an annular gap, channel or groove, or a projection in one or both surfaces such as an arbor, a small pin, or the like.

In a preferred embodiment, the stroke of the piston is larger than the distance between the end face of the piston in its rest position and the sealing surface.

As used herein, the term "tightly adjacent" means that a planar contact occurs between the end face of the piston and the sealing surface, and includes the possibility, as discussed above, of a small portion of the contact being non-planar, due to the presence of the aforementioned depressions or projections. A thin element such as a film or a plate having a central opening, in the form of an apertured diaphragm of the type known in optics, can thus be disposed between the end face of the cylinder and the sealing surface. Pumping of liquid substantially free of dead space is achieved in the present invention by disposing the moveable element of the check valve at the output of the pump, and by adapting the sealing surface of the moveable element to the shape of the end face of the piston, so that the sealing surface presses tightly adjacent the end face of the piston when the piston is approaching the end of its output stroke. Due to such tight adjacency, neither liquid nor air is situated between the end face of the piston and the sealing surface when the piston completes its output stroke. When the piston slides back toward the input during its return stroke, the sealing surface of the moveable element of the check valve remains tightly adjacent the end face of the piston until the sealing surface is stopped, for example by a cup point. The piston continues to move in the direction toward the input chamber, so that the pump chamber can fill with liquid from a reservoir which flows through the gap between the cylinder wal and the piston. Any gas bubbles which may have been present were forced out through the pump output, and are prevented from returning to the pump chamber by the check valve.

The reciprocating pump disclosed herein is particularly suitable for use in a medication dosage device having a medication reservoir maintained at an underpressure.

DESCRIPTION OF THE PREFERRED EMBODIMENTS

Figure 1:
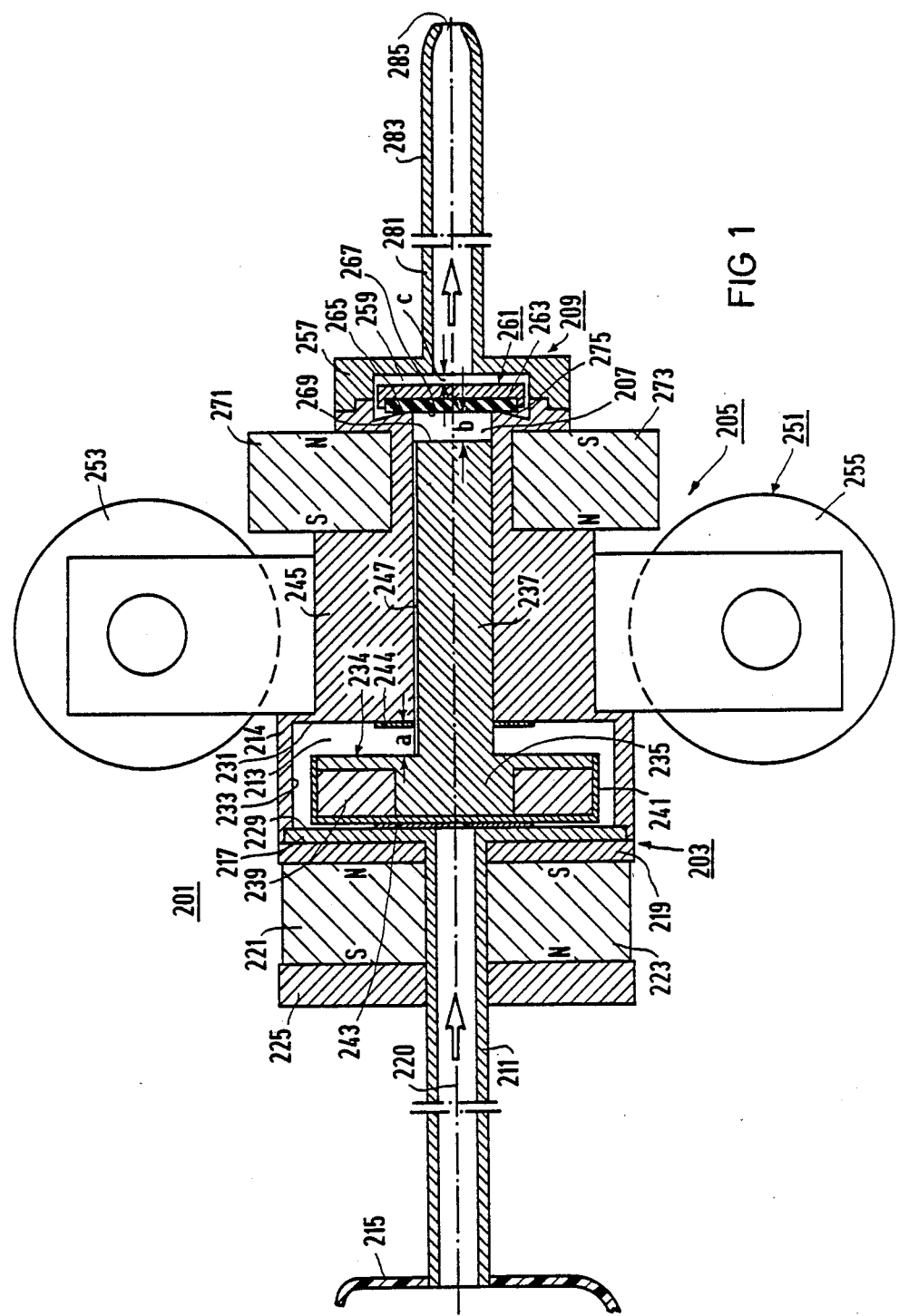
FIG. 1 is a side sectional view of a reciprocating pump constructed in accordance with the principles of the present invention with the piston disposed at a rest position.

The basic elements of a reciprocating pump 201 constructed in accordance with the principles of the present invention are shown in FIG. 1. The pump 201 conveys a volume of less than 10 $\mu$liters, particularly about 1 $\mu$liter. The reciprocating pump 201 generally consists of an input system 203 including a magnetic restoring spring, a pump system 205 including a pump chamber 207, and an outlet system 209 including a moveable element 261 forming a part of a check valve.

The input system 203 includes a fluid passage having an input line 211 and a cylindrical input chamber 213 in a housing 214. A medication reservoir 215 is connectable to the input line 211. The medication reservoir 215 is preferably charged with an underpressure relative to the atmosphere, for example, 300 mbar. The reservoir 215 may contain, for example, insulin. The input line 211 discharges via a flange 217 into the input chamber 213. The input chamber 213 has a significantly enlarged cross section compared to the cross section of the input line 211. As an alternative to the embodiment shown in FIG. 1, it is possible to omit the input line 211, and to make the input chamber 213 a component part of the medication reservoir.

A non-magnetic, cylindrical carrier 219 is seated around an end of the input line 211 approaching the input chamber 213. The carrier 219 has two permanent magnets 221 and 223 symmetrically mounted thereon relative to an axis 220. The permanent magnets 221 and 223, for example, may be cylindrical or cubic, and have the respective indicated polarities S-N and N-S. The two magnets 221 and 223 may alternatively be replaced by a single permanent magnet arranged axially around the end of the input line 211. The permanent magnets 221 and 223 supply a restoring force for the pump system 205. As described in detail below, the magnets serve as a spring system or a restoring spring for returning or urging the piston 237 to a quiescent or rest position. A magnetic return element 225 consisting of, for example, a cylinder of soft iron is disposed against the respective poles of the magnets 221 (the S pole) and 223 (the N pole) which face away from the remainder of the pump.

The input chamber 213 is limited by an end face 229 of the flange 217, and by an end face 231 and a cylindrical interior wall 233 of the housing 214. An axially displaceable cylindrical armature 234 is disposed in the input chamber 213. The armature 234 is mounted on an armature carrier 235 which merges into a longer piston 237, which is smaller in diameter than the armature. It is also possible to construct a separate armature carrier 235 and a separate piston 237, and to connect those separate elements by suitable attachment means.

An annular armature element 239 is secured to the armature carrier 235. The armature element 239 is inverted over the core of the armature carrier 235, which merges into the piston 237. The armature element 239 consists of magnetic material, for example, soft iron. A cylindrical can or capsule 241 partially surrounds the armature carrier 235 and completely surrounds the armature element 239. To avoid interaction with the liquid medication to be conveyed by the reciprocating pump 201, the capsule 241 is placed around the armature element 239 and is connected at the edge to the armature carrier 235, so that a complete encapsulation of the armature element 239 is achieved.

The permanent magnets 221 and 223 disposed outside of the input chamber 231 constantly exert a force on the armature 234 which attracts the armature 234, together with the piston 237, in the direction toward the input line 211, but such attraction does not close the input opening in the flange 217. For this purpose, a stop 243, such as a thin, annular, centrally disposed plate, is provided at the end face 239 of the flange 217 to limit the movement caused by the attractive force of the magnets 221 and 223. Another stop 224, such as a thin, axially disposed ring, is attached to the other end face 231 of the input chamber 213. When the armature 234 is disposed at the left end face 229, the piston 237 is in its rest position. The distance between the rear of the armature 234 and the end face 231 (or possibly the stop 244, if present) is precisely defined, and amounts to "a." The two permanent magnets 221 and 223 together with the carrier 219 and the return element 225 are preferably displaceable in the direction of the longitudinal axis 220, so that the restoring force acting on the armature 234, and thus on the piston 237, is continuously adjustable to a desired value.

The piston 237 is longitudinally displaceable in the portion of the housing 214 which serves as a cylinder 245. A gap 247, preferably an annular gap, is present between the cylinder 245 and the piston 237. The liquid medication is conveyed through this gap from left to right when the piston 237 is reset to its rest position, as described in greater detail below.

The armature 234 simultaneously serves as an armature for an electromagnetic drive system 251 arranged at the cylinder 245. This drive system includes two electromagnetic coils 253 and 255. Upon excitation of these coils with a current, a magnetic field of sufficient magnitude to influence the armature 234 is generated. As a result, the armature 234 and the piston 237 are displaced in the direction toward the discharge system 209, until the armature 234 strikes against the right end face 231, or against the stop 244.

An outlet chamber 259 is disposed downstream directly behind the pump chamber 207, partly in the housing 214 and partly in a carrier flange 257. A moveable, cylindrical valve element 261 is contained within the outlet chamber 259. The cylindrical valve element 261 is part of a check valve. The valve element 261 has a larger diameter than the piston 237. The valve element 261 is formed of two components, and includes a closing element 263 on which a sealing disk 265, having a sealing surface 267, is attached at the piston side. The sealing disk 265 may, for example, consist of an inert plastic.

The pump chamber 207 is limited downstream by the axial region of the sealing surface 267. The pump chamber 207 is further limited by the interior cylindrical surface of the housing 245, and by the end face 269 of the piston 237. In the rest position of the piston 237 shown in FIG. 1, the distance between the sealing surface 267 closing the pump chamber 207 and the end face 269 is precisely defined, and amounts to "b." The distance b is less than or equal to the aforementioned distance a, such that $a = b + \Delta b$, wherein $\Delta b$ is small and is in the range of zero to 0.05 mm. The distance "c" also shown in FIG. 1, which describes the maximum possible movement of the valve element 261, is somewhat larger than $\Delta b$. In an insulin dosing device, for example, $c = 0.3$ mm.

The closing element 263 of the valve element 261 consist of magnetic material, and functions as an armature. The closing element 263 in combination with two permanent magnets 271 and 273 form another magnetic spring system. The permanent magnets 271 and 273 surround the outside of the pump chamber 207 and are disposed about the axis 220 with the respectively indicated polarities S-N and N-S. An annular permanent magnet may alternatively be used instead of the two magnets 271 and 273. The magnetic spring system hold the valve element 261 in a rest position. The sealing surface 267 of the sealing disk 265 is in this position pressed against the input opening of the pump chamber 207, which may be in the form of a cup point 275. A liquid-tight and gas-tight closure is formed when the sealing surface 267 is forced against the cup point 275.

It is alternatively possible to use a mechanical spring system to provide the pressing force of the sealing surface 267 against the cup point 275 in the rest state of the valve element 261. Such a mechanical spring system (not shown) should be disposed in that part of the outlet chamber 259 closest to the output side. For example, such a spring system may be formed by a coil spring disposed in the region between the rear of the element 263 and the front side of the flange 257.

It is also possible, although not shown in FIG. 1, to mount the permanent magnets 271 and 273 so as to be displaceable along the longitudinal axis 220 of the cylinder 245. This permits the restoring force acting on the valve element 261 to be set after the reciprocating pump 201 is completely assembled. Such adjustment capability in no way changes the amount of dead space in the pump chamber 207.

A discharge line 281 merging into a catheter 283, having an outlet opening 285, is connected to the outlet chamber 259 by an outlet flange 257. The outlet opening 285 is positioned at a selected location in a patient during implantation. The catheter 283 may be either directly connected to the outlet chamber 259, or connected thereto via a conduit of suitable length.

During operation of the reciprocating pump 201, the piston 237 is moved toward the right, out of the illustrated rest position, by the influence of the electromagnetic field generated by the coils 253 and 255. A substantial overpressure thereby arises acting on the medication in the pump chamber 207. As soon as the force exerted on the moveable valve element 261 by this overpressure exceeds the restoring force of the magnetic spring system formed by the magnets 271 and 273 and the closing element 263, the sealing surface 267 of the valve element 261 is forced off the cup point 275. A valve gap thus forms between the valve element 261 and the cup point 275. The liquid medication, for example, insulin, is expressed into the catheter 283 via the outlet line 281 against the catheter pressure and the opening pressure of the valve element 261. The liquid medication contained in the pump chamber 207 flows through the valve gap, through the outlet chamber 259, and through the catheter 283 in the direction of arrow. As the piston 237 approaches its extreme (right-most) position in its stroke, the overpressure in the pump chamber 207 is reduced due to the medication flowing out of the chamber 207. When the maximum or extreme stroke position is reached, the end face 269 of the piston 237 lies tightly adjacently against the sealing surface 267 of the valve part 261. As stated above, the term "tightly adjacent" as used herein means that neither medication liquid nor gas bubbles can be situated between the two surfaces 269 and 267. As a consequence of the selected dimensioning of a greater than or equal to b, the valve element 261 and the sealing disk 265 can be forced off of the cup point 275 by the amount Δb. At least one of the two surfaces 267 or 269 is preferably provided with a projection or a depression to later enable easy detachment during the return stroke of the piston 237.

If, by contrast, a is selected slightly smaller than or equal to b, as soon as the force exerted on the moveable valve element 261 by the overpressure in the pump chamber 207 falls below the magnetic restoring force of the spring system (magnets 271 and 273 and the closure element 263) the moveable valve element 261 again moves onto the cup point 275, closing the valve gap.

As described above, it is important that the end face 269 of the piston 237, when the piston 237 is at its extreme output stroke position, be located at the same level which the sealing surface 267 assumes in its rest position, or that the end face 269 of the piston 237 move slightly beyond this level by the amount Δb, so that the pump chamber 207 is substantially free of dead space. Given a small displacement volume of, for example, 1 microliter, a substantially constant conveying volume is maintained by simultaneously permitting air or other gap bubbles to be easily conveyed through the pump. This is also true given an underpressure in the medication reservoir 215, or given an overpressure in the catheter 283, for example, as a consequence of blockage of the catheter 283, against which the pump 201 must pump. The pump operation is therefore not brought to a standstill even in the presence of gas bubbles in the liquid medication to be conveyed.

After the coils 253 and 255 are de-energized, the piston 237 moves back to the position as illustrated in FIG. 1, by the magnetic field generated by the permanent magnets 221 and 223 acting on the armature element 239.

As discussed above in connection with the other magnet system, this magnet system may alternatively be a spring magnet system or someother type of mechanical return (not shown).

The return movement of the piston 237 to the position shown in FIG. 1 detaches the surfaces 267 and 269, so that an underpressure is generated in the pump chamber 207. When the absolute value of this underpressure is lower than the underpressure in the medication reservoir 215, a pressure gradient arises. The liquid medication is thereby drawn into the pump chamber 207 against the underpressure in the medication reservoir 215 due to the greater underpressure in the pump chamber 207. The medication flows through the gap 247 between the piston 237 and the cylinder 245. The valve element 261 and the cup point 275 act as a check valve.

The advantage of the reciprocating pump 201 shown in FIG. 1 is its capability of conveying small volumes of liquid from an underpressurized reservoir 215 with high dosage precision. The functioning of the pump is not degraded by the presence of gas bubbles in the medication conveying passage. The reciprocating pump 201 is preferably used in an implantable insulin dosage device.

Figure 2:
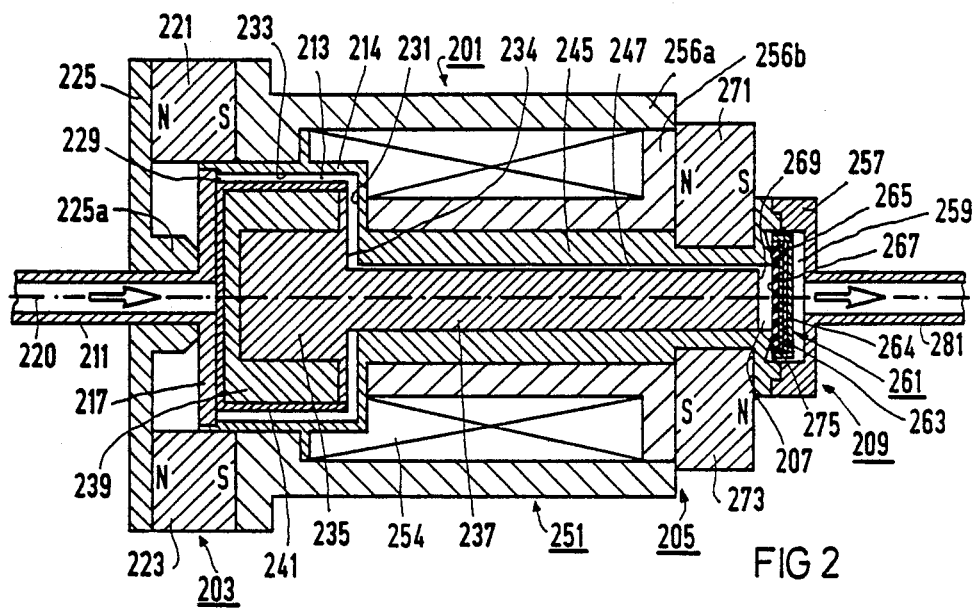
FIG. 2 is a side sectional view of another embodiment of a reciprocating pump constructed in accordance with the principles of the present invention.

Another embodiment of a reciprocating pump constructed in accordance with the principles of the present invention is shown in FIG. 2. Elements of the embodiment of FIG. 2 identical to those in FIG. 1 are provided with the same reference symbols. In contrast to the embodiment of FIG. 1, the embodiment of FIG. 2 does not have a carrier 219. Instead, the return element 225 is provided with a centrally disposed boss 225a. Additionally, in the embodiment of FIG. 2 the armature element 239 is in the form of a cylindrical cap or cover. Also departing from the embodiment of FIG. 1, the embodiment of FIG. 2 does not employ coils 253 and 255. Instead a coaxially disposed drive system 254, such as an electromagnet, is used. This is accommodated in a two-piece housing consisting of halves 256a and 256b seated on the cylinder 245. The embodiment of FIG. 2 permits a simple assembly of the pump. The closure element 263 of the valve element 261 in the embodiment of FIG. 2 is titanium encapsulated, as shown in greater detail in the enlarged view of FIG. 3.

Figure 3:
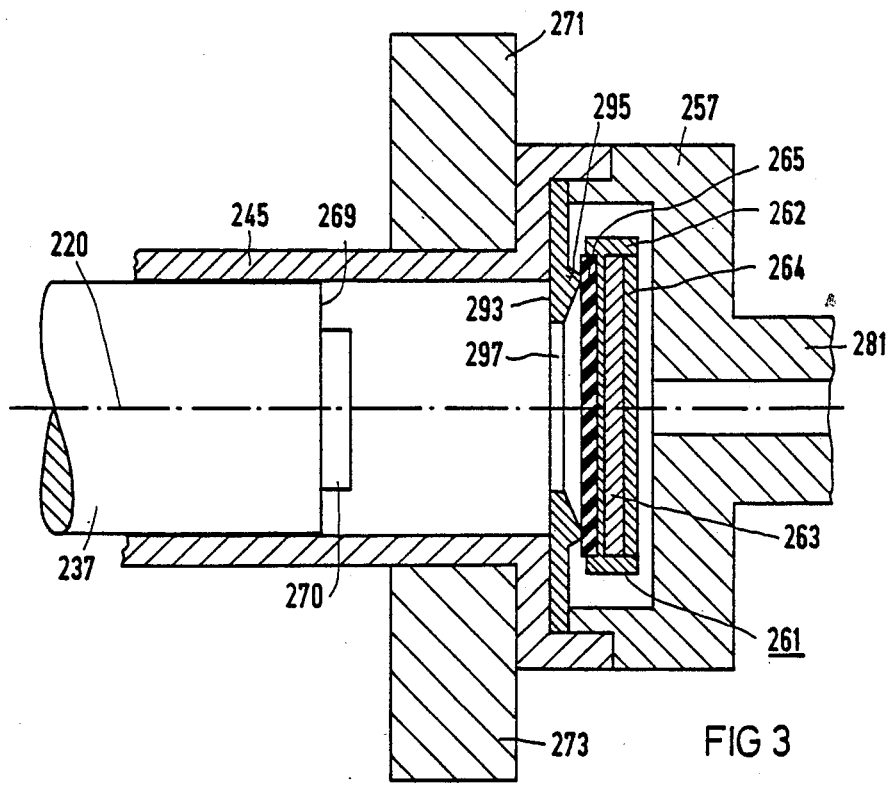
FIG. 3 is an enlarged side sectional view of the portion of the reciprocating pump in either of the above embodiments surrounding the check valve.

As shown in FIG. 3, the moveable valve element 261 consists of a plurality of elements. These include an armature carrier 265 having cylindrical receptacles on both sides thereof. The carrier 265 consists of titanium, and receives the sealing disk 265 at the piston side, and an armature disk 263 at the outlet side. The armature disk 263 consists of magnetic material. The outlet side of the disk 263 is covered by a cover disk 264, also consisting of titanium welded gas-tight to the armature carrier 262. The armature disk 263 is thus completely encapsulated by titanium on all sides.

As also shown in FIG. 3, a diaphragm 293 having a central aperture therein is retained by the flange 257 at the end face of the cylinder 245. The diaphragm 293 is thus disposed between the end face 269 of the piston 237 and the sealing surface 267. At its outlet side, the diaphragm 293 has an annular bead or rim 295 forming the aforementioned cup point to facilitate lifting of the valve element 261. To maintain the dead space small, the end face 269 of the piston 237 is provided with a displacing projection 270. The projection 270 is cylindrical, and disposed concentrically relative to the axis 220. The projection 270 fits into the opening 297 of the diaphragm 293 and performs the same function as the piston surface 269 discussed above.

Although modifications and changes may be suggested by those skilled in the art it is the intention of the inventors to embody within the patent warranted hereon all changes and modifications as reasonably and properly come within the scope of their contribution to the art.

We claim as our invention:

1. A reciprocating pump for an implantable medicaton dosage device comprising:
    a housing have a fluid conveying passage with a piston consistig at least in part of magnetically attractive material and having a planar end face disposed in said passage, said passage terminating in an outlet;

first magnetic means for moving said piston in said passage through an output stroke to force fluid through said outlet;

second magnetic means for moving said piston in said passage through a return stroke;

a valve disposed at said outlet of said passage having a moveable element having a portion consisting of magnetic material;

a permanent magnet spring system disposed to act on said magnetic material portion of said moveable element for normally forcing said moveable element against said outlet to block fluid flow through said passage;

said moveable element of said valve having a planar surface disposed for pressing tightly adjacent said end face of said piston for at least a portion of said output stroke, at least one of said surface of said moveable element or said end face of said piston having a non-planar region; and said piston assuming a rest position in said housing at an end of said return stroke with a distance between said end face of said piston and said surface, and said piston and said passage being cooperatively dimensioned so that said output stroke is longer than said distance, thereby lifting said moveable element away from said outlet during said output stroke.

2. A reciprocating pump as claimed in claim 1, further comprising a cup point surrounding said outlet against which said sealing surface is disposed when said moveable element is forced against said outlet by said permanent magnet spring spring system.

3. A reciprocating pump as claimed in claim 1, wherein said moveable element consists of a carrier and a disk attached to said carrier, said disk facing said outlet and forming said sealing surface.

4. A reciprocating pump as claimed in claim 1, further comprising means for forming in combination with said housing an outlet chamber in which said valve is contained.

5. A reciprocating pump as claimed in claim 1, wherein the difference between said length of said output stroke and said distance is about 0.05 mm.

6. A reciprocating pump as claimed in claim 1, wherein said first magnetic means is an electromagnetic means for moving said piston through said output stroke.

7. A reciprocating pump as claimed in claim 1, wherein said second magnetic means is a permanent magnetic means for moving said piston through said return stroke.

8. A reciprocating pump as claimed in claim 7, further comprising means for mounting said permanent magnet means for displacement of said permanent magnet means relative to said housing.

9. A reciprocating pump as claimed in claim 1, wherein said passage has an inlet, and further comprising means for generating a pressure differential between said inlet and said outlet of said passage, with said inlet at a lower pressure than said outlet.

10. A reciprocating pump as claimed in claim 1, further comprising a diaphragm disposed between said outlet and said sealing surface, said diaphragm having an opening in registry with said passage through which said end face of said piston and said fluid pass.

11. A reciprocating pump as claimed in claim 10, wherein said end face of said piston has a projection which extends through said opening of said diaphragm.

* * * * *